US009733177B2

(12) United States Patent
Sharples et al.

(10) Patent No.: US 9,733,177 B2
(45) Date of Patent: Aug. 15, 2017

(54) METHOD AND SYSTEM FOR OPTICAL EVALUATION, AND OPTICAL DETECTOR

(71) Applicant: THE UNIVERSITY OF NOTTINGHAM, University Park, Nottingham (GB)

(72) Inventors: Stephen Sharples, Nottingham (GB); Roger Light, Nottingham (GB)

(73) Assignee: University of Nottingham, Nottingham (GB)

(*) Notice: Subject to any disclaimer, the term of this patent is extended or adjusted under 35 U.S.C. 154(b) by 371 days.

(21) Appl. No.: 14/362,392

(22) PCT Filed: Nov. 30, 2012

(86) PCT No.: PCT/GB2012/052965
§ 371 (c)(1),
(2) Date: Jun. 2, 2014

(87) PCT Pub. No.: WO2013/079960
PCT Pub. Date: Jun. 6, 2013

(65) Prior Publication Data
US 2015/0260640 A1    Sep. 17, 2015

(30) Foreign Application Priority Data
Dec. 2, 2011 (GB) .................................. 1120774.3

(51) Int. Cl.
*G01N 21/17* (2006.01)
*G01H 9/00* (2006.01)
*H01L 27/146* (2006.01)

(52) U.S. Cl.
CPC .......... *G01N 21/1702* (2013.01); *G01H 9/00* (2013.01); *H01L 27/14609* (2013.01); *G01N 2201/0612* (2013.01); *G01N 2201/0675* (2013.01)

(58) Field of Classification Search
CPC ................ G01H 9/00; G01N 21/1702; G01N 2201/0675; G01N 2201/0612; H01L 27/14609
See application file for complete search history.

(56) References Cited

U.S. PATENT DOCUMENTS 3,700,903 A * 10/1972 Adler .................... G01H 9/002
250/222.1
4,032,801 A  6/1977 Fulkerson
(Continued)

FOREIGN PATENT DOCUMENTS

CN    101055265 A    10/2007
JP    S6036922 A    2/1985
(Continued)

*Primary Examiner* — John Lee
(74) *Attorney, Agent, or Firm* — Quarles & Brady LLP

(57) ABSTRACT

An optical detector comprises a plurality of pixels, each pixel comprising a photodiode operable to detect light incident on that pixel and to generate a signal indicative of an intensity of that light. The plurality of pixels comprises a plurality of pixel pairs, and for each pixel pair, in a configuration mode, the detector is arranged to compare the signal generated by a first pixel of the pair with the signal generated by a second pixel of the pair. A method of optical detection is also described, as is a system incorporating the described optical detector.

23 Claims, 8 Drawing Sheets

(56) References Cited

U.S. PATENT DOCUMENTS

| | | | |
|---|---|---|---|
| 4,567,769 A * | 2/1986 | Barkhoudarian | G01H 9/006 374/5 |
| 4,978,861 A * | 12/1990 | Sabater | G01B 11/303 250/559.23 |
| 5,013,919 A | 5/1991 | Solomon | |
| 5,585,921 A * | 12/1996 | Pepper | G01N 29/075 356/432 |
| 5,760,904 A * | 6/1998 | Lorraine | G01B 11/16 356/513 |
| 6,087,652 A * | 7/2000 | O'Meara | G01D 5/26 250/208.1 |
| 6,097,477 A * | 8/2000 | Sarrafzadeh-Khoee | G01B 11/162 356/35.5 |
| 6,115,127 A * | 9/2000 | Brodeur | G01B 17/00 356/432 |
| 6,144,685 A * | 11/2000 | Iwasa | B41J 2/45 372/24 |
| 7,078,673 B1 | 7/2006 | Afriat | |
| 7,088,455 B1 * | 8/2006 | Kirkpatrick | G01N 21/1717 356/502 |
| 7,293,463 B2 * | 11/2007 | Suzuki | G01N 29/2418 356/499 |
| 7,324,665 B2 * | 1/2008 | Rohaly | G01P 5/001 382/107 |
| 7,738,014 B2 | 6/2010 | Kwak et al. | |
| 7,957,006 B2 * | 6/2011 | Aharoni | G01H 9/00 356/502 |
| 8,006,558 B2 * | 8/2011 | Clark | G01N 29/0681 73/597 |
| 8,643,846 B2 * | 2/2014 | Santhanakrishnan | G01H 9/00 356/499 |
| 2005/0062720 A1 | 3/2005 | Rotzoll | |
| 2005/0210982 A1 * | 9/2005 | Pepper | G01H 9/00 73/602 |
| 2006/0215175 A1 * | 9/2006 | Yacoubian | G01N 21/1717 356/502 |
| 2009/0025480 A1 * | 1/2009 | Aharoni | G01H 9/00 73/655 |
| 2009/0149750 A1 * | 6/2009 | Matsumura | A61B 5/0048 600/438 |
| 2009/0272882 A1 * | 11/2009 | Rabner | H01L 27/148 250/214 A |
| 2010/0319455 A1 * | 12/2010 | Ihn | G01N 29/069 73/603 |
| 2011/0197679 A1 * | 8/2011 | Kono | G01N 29/28 73/632 |
| 2015/0260640 A1 * | 9/2015 | Sharples | G01H 9/00 250/208.2 |

FOREIGN PATENT DOCUMENTS

| | | |
|---|---|---|
| JP | 7270323 | 10/1995 |
| WO | 03049018 A1 | 6/2003 |

* cited by examiner

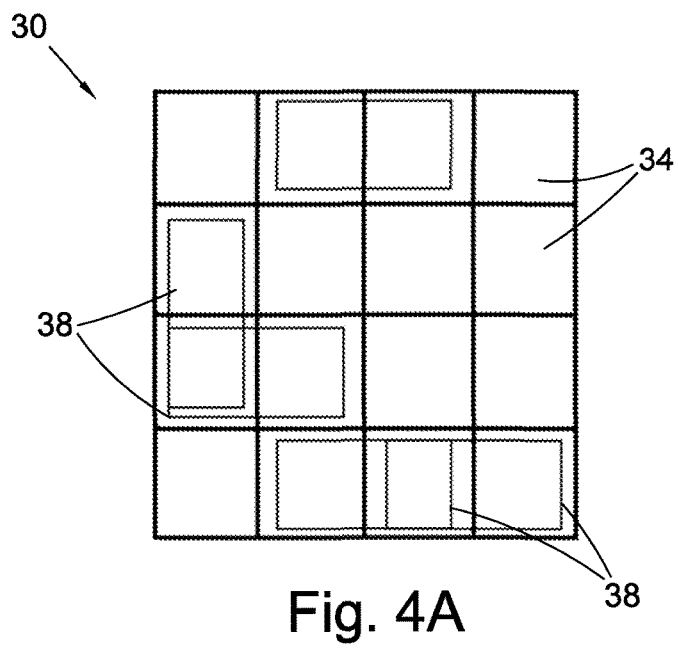
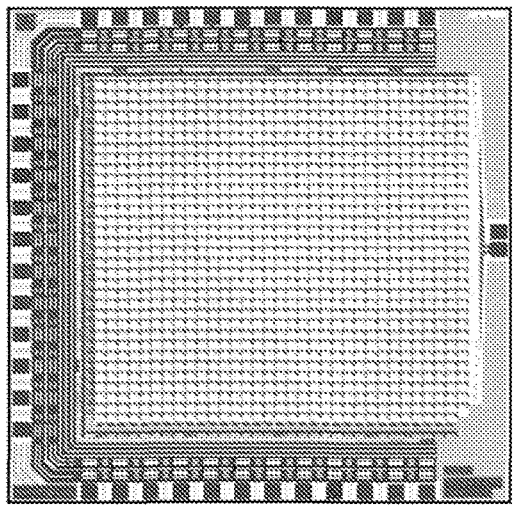
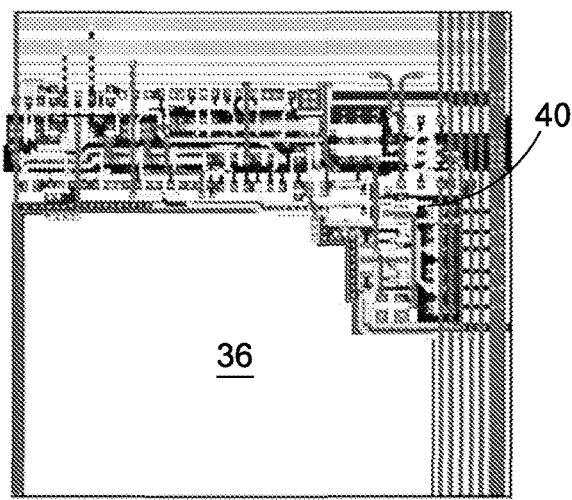
Fig. 4A
Fig. 4B
Fig. 4C

METHOD AND SYSTEM FOR OPTICAL EVALUATION, AND OPTICAL DETECTOR

This Application is a 371 application of PCT/GB2012/052965, filed Nov. 30, 2012, which claims priority to GB1120774.3, filed Dec. 2, 2011, the entire contents of which are incorporated herein in their entirety by reference.

The present invention relates to a method and system for optical evaluation, as well as to optical detectors for use in such methods and systems. The present invention relates particularly, but not exclusively, to optical detection of ultrasonic waves on the surface of materials.

Ultrasonics is widely used for testing materials for defects, wear, cracks etc and has the key advantage that it allows inspection of optically opaque materials. A problem with conventional (non-laser) ultrasonics is that it requires contacting transducers to generate and detect the ultrasonic waves. This means the methods are unsuitable for inaccessible or hazardous environments. Laser ultrasonics overcomes these problems by using a laser to generate and detect the sound waves. One laser generates the sound by heating the sample which induces thermal expansion, which, in turn, produces a sound wave, typically including a surface acoustic wave (SAW) which travels across the surface of the material under test. Such a sound wave can be detected with a second laser system which measures the small changes in the shape of the surface as the sound wave passes under it.

Laser ultrasonics is, however, not without its own problems, the main one being that when the sample we wish to examine is 'rough' as many engineering components are (rough here only means sufficiently unpolished that it is not a good mirror) the light is scattered randomly and conventional optical techniques will not detect the presence of sound waves passing under the optical beam.

We propose herein an optical detector which may be used in laser ultrasonic evaluation of rough as well as smooth surfaces. The optical detector is also applicable for use in other circumstances.

According to a first aspect of the invention there is provided an optical detector comprising a plurality of pixels, each pixel comprising a photodiode operable to detect light incident on that pixel and to generate a signal indicative of an intensity of that light, wherein the plurality of pixels comprises a plurality of pixel pairs, and wherein for each pixel pair, in a configuration mode, the detector is arranged to compare the signal generated by a first pixel of the pair with the signal generated by a second pixel of the pair.

The optical detector may be operable to use the comparison to determine whether the intensity of light incident on the first pixel of the pair is higher (or lower) than the intensity of light incident on the second pixel of the pair.

The optical detector may comprise a first output and a second output, and the signal indicative of intensity generated by the first pixel may be connected to either the first output or the second output depending on the result of the comparison. For example, if the first intensity signal is higher than the second intensity signal, the signal from the first pixel may be connected to the first output. Conversely, if the first intensity signal is lower than the second intensity signal, the signal from the first pixel may be connected to the second output.

The comparison may be performed simultaneously and in parallel over the plurality of pixel pairs.

The plurality of pixels may comprise an array, and in use the signal indicative of intensity generated by each pixel in an active area of the array may be connected to either the first output or the second output.

The optical detector may further comprise an experiment mode in which the signals indicative of intensity received at the first output are summed to produce a first composite intensity signal, and in which the signals indicative of intensity received at the second output are summed to produce a second composite intensity signal.

The second composite intensity signal may be subtracted from the first composite intensity signal (or vice versa).

Each pair of pixels may comprise a pair of adjacent pixels. The arrangement of the pairs may be periodic, such that the first pixel of each pair always has the same spatial relation with respect to the second pixel of that pair.

The pairs may overlap, such that the first pixel in one pair comprises the second pixel in an adjacent pair.

The plurality of pixels may be provided in a regular planar array having a first axis and a second axis which is perpendicular to the first axis. The comparison may be performed based on pairs arranged in alignment with the first axis or the second axis. The comparison may be switchable/operable to be switched between a comparison of pairs in the first axis and a comparison of pairs in the second axis.

The comparison may be effected by comparison means coupled between the first and second pixels of a respective pair. Comparison means may be provided between a first pixel and a plurality of neighbouring pixels, so that the intensity signal of the first pixel may be compared with the intensity signal of any one of the plurality of neighbouring pixels.

The comparison may comprise a comparison of currents generated by the photodiodes of the first and second pixels of a respective pair.

The plurality of pixels may comprise an array having an active area and a dummy area, and pixels of the dummy area might not have their intensity signals connected to the first or second output.

The detector may be switched between configuration and experiment modes regularly, for example at a regular frequency.

According to a second aspect of the invention there is provided an optical detector comprising a plurality of pixels, each pixel comprising a photodiode operable to detect light incident on that pixel and to generate a signal indicative of an intensity of that light, wherein the detector comprises a first output and a second output, and wherein the detector is operable such that the signal indicative of intensity generated by each pixel is connected either to the first output or to the second output, and wherein signals indicative of intensity received at the first output are summed to produce a first composite intensity signal, and signals indicative of intensity received at the second output are summed to produce a second composite intensity signal.

The second composite intensity signal may be subtracted from the first composite intensity signal (or vice versa).

The output to which each pixel is connected may be selected (e.g. programmed) by a user. The output to which each pixel is connected may be selected based on a comparison with another pixel of the plurality of pixels, as described above with reference to the first aspect of the invention, According to a third aspect of the invention there is provided an optical evaluation system comprising a detection optical source, detection optics and an optical detector as described above in respect of the first or second aspect of the invention, or any of the dependent clauses.

The optical evaluation system may further comprise an excitation optical source operable to generate sound waves in a sample under test, and may further comprise optical imaging means such as a spatial light modulator to shape optical radiation generated by the excitation optical source. The optical imaging means may be operable to shape the optical radiation so as to cause the sound waves to come to a focus.

According to a further aspect of the invention there is provided a method of operating an optical detector having a plurality of pixels, each comprising a photodiode operable to detect light incident on that pixel and to generate a signal indicative of an intensity of that light, the method comprising grouping a plurality of pixels into pairs, and, in a configuration mode, comparing the signal generated by a first pixel of the pair with the signal generated by a second pixel of the pair.

The method may further comprise using the comparison to determine whether the intensity of light incident on the first pixel of the pair is higher than the intensity of light incident on the second pixel of the pair.

The method may further comprise connecting the signal indicative of intensity generated by the first pixel to either a first detector output or a second detector output depending on the result of the comparison.

The method may further comprise summing the signals indicative of intensity received at the first output to produce a first composite intensity signal, and summing the signals indicative of intensity received at the second output to produce a second composite intensity signal, and may further comprise subtracting the second composite intensity signal from the first composite intensity signal (or vice versa).

The comparison may be performed simultaneously and in parallel over the plurality of pixel pairs.

An example of the invention will now be described, by way of example only, with reference to the following drawings:

FIG. 1 shows schematically an optical evaluation system, and in particular a laser ultrasonic evaluation system;

FIG. 2 schematically shows the generation of an ultrasonic wave (SAW) in the system of FIG. 1;

FIG. 3 schematically depicts reflected light falling on a prior art knife edge detector for A, a smooth surface; and B, a rough surface;

FIG. 4 shows A, a schematic illustration of an optical detector; B, the layout of an optical detector chip; and C, the layout of a single pixel of the detector chip of picture B;

Figure 8:
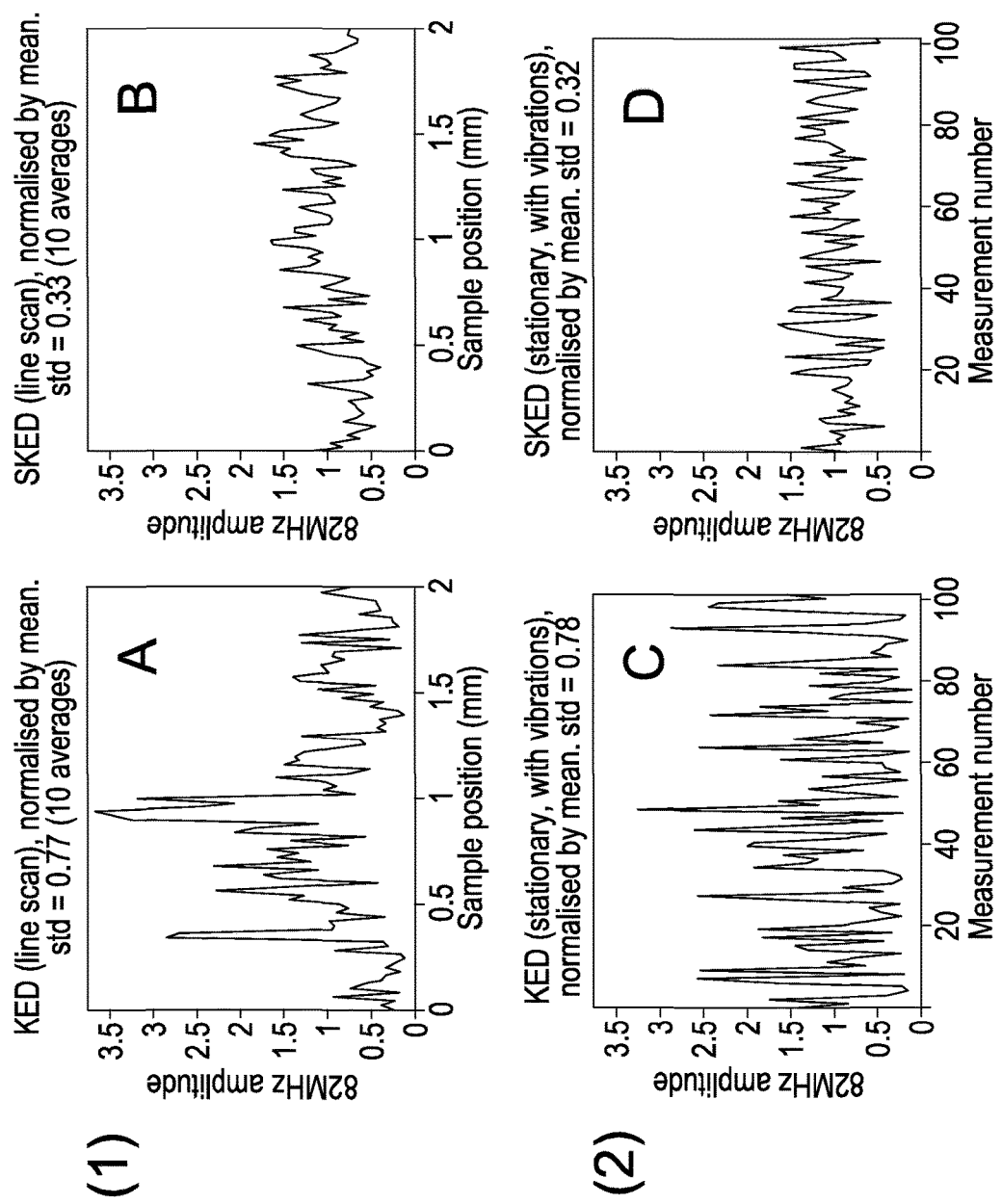
Figure 9:
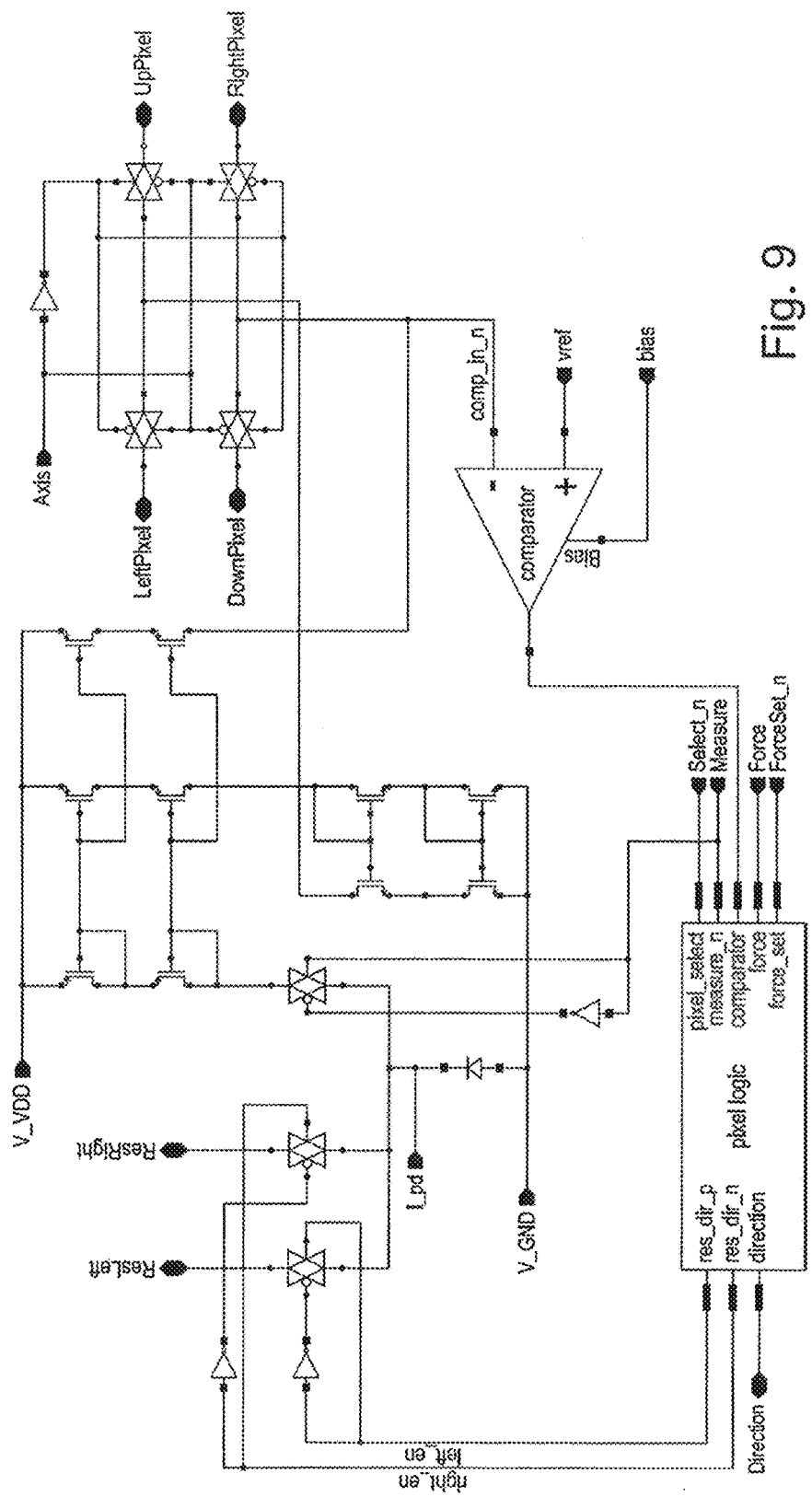
Figure 10:
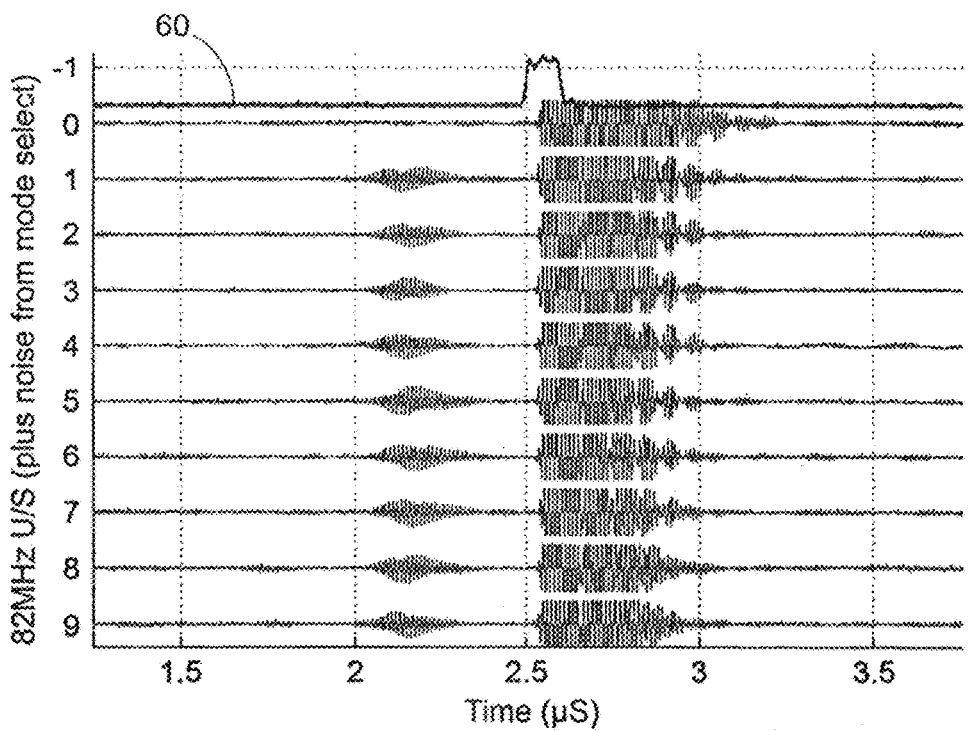
Figure 11:
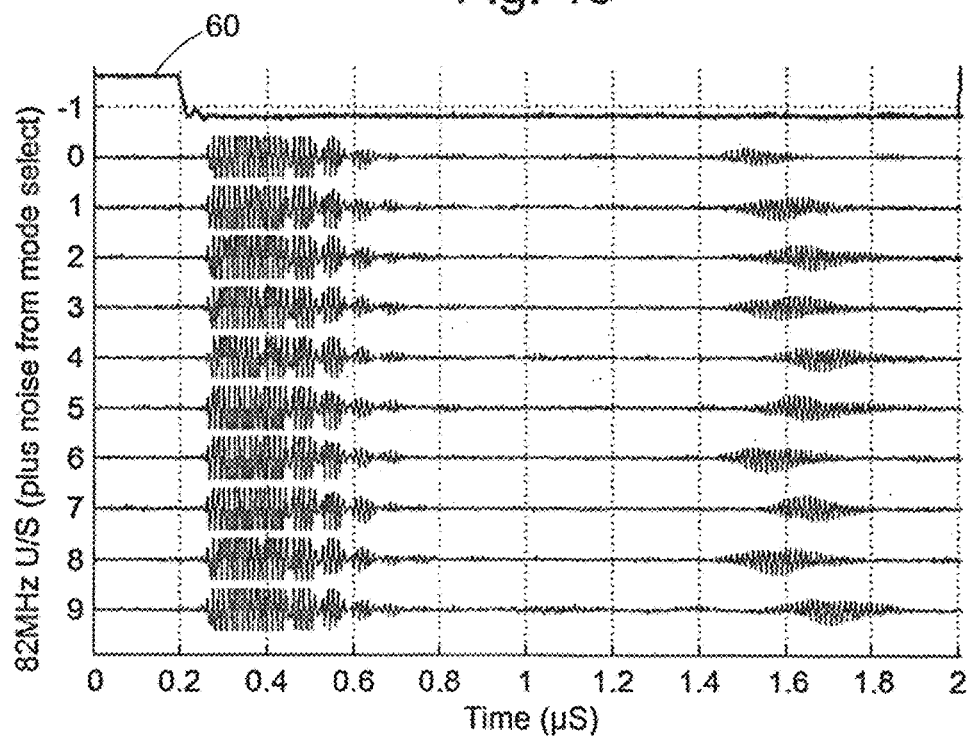

FIG. 8 shows (1) a comparison between a scan of a rough sample produced by a prior art knife edge device (picture A), and a scan of the same rough sample produced by an optical detector of the type described herein (picture B); and (2) a similar comparison when the sample under test is subjected to mechanical vibrations (picture C being the prior art knife edge device and picture D being an optical sensor as described herein);

FIG. 9 is a more detailed circuit schematic for a pixel;

FIG. 10 illustrates how a configuration time for the optical detector can be determined; and FIG. 11 illustrates how a minimum time between adapting and measuring can be determined.

One of the simplest and most effective detectors for the detection of ultrasound by lasers is the knife edge detector. A knife edge detector takes advantage of the fact that a sound wave passing across the surface of a sample causes the surface of the sample to move. If an optical beam is directed onto the surface, the light of the beam is reflected from the surface and is deflected by a tiny angle as the sound wave passes. Optics, in the form of an array of lenses, converts the deflection to a horizontal movement of the beam synchronous with the passing sound wave, which can then be detected by a light-sensitive detector. It is possible to detect the beam deflection using either a conventional knife edge, or a split photodiode 2 as shown in FIG. 3.

Figure 3A:
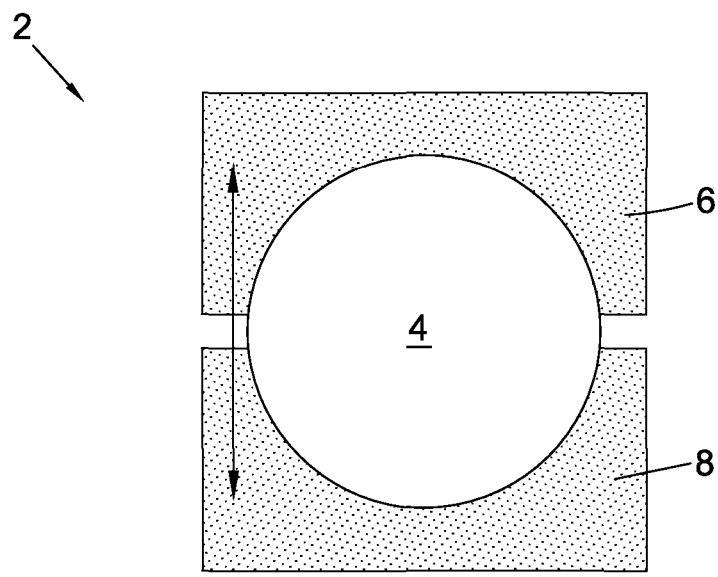
Figure 3B:
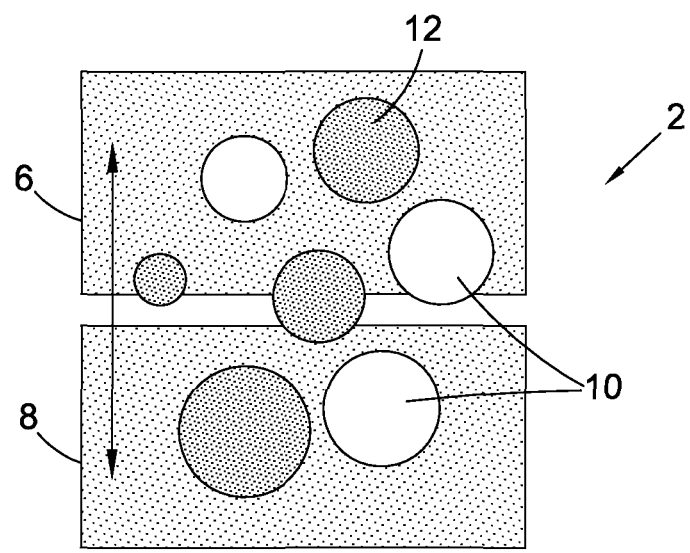

For a smooth surface, the reflected light focuses to a well-defined specular reflection in the form of disc 4 shown in the left hand image (picture A) of FIG. 3. As the sound wave passes, the disc of light moves vertically across the detector. The 'split' detector 2 subtracts signal from the top photodiode 6 from the signal from the bottom photodiode 8. Thus a positive signal is obtained when the beam moves from top to bottom and a negative signal is obtained when the movement is from bottom to top. Thus the movement of the sound wave is tracked in a simple and effective way by the oscillating beam when the sample is smooth.

When the sample is rough, however, the light is no longer a neat disc but is 'speckled', as shown in picture B of FIG. 3. 'Speckled' as used herein means the reflected light forms a group of light 10 and dark 12 patches. The light and dark patches move together as an ultrasonic wave crosses the surface of the sample. This means that as the beam moves from top to bottom of the photodiode shown in FIG. 3, a simple subtraction between the two halves will not give a useful signal because some parts of the top/bottom subtraction will give a positive number and others will give a negative number, so that on average there will be no signal at all.

'Rough' surfaces, as referred to herein typically mean surfaces which are not sufficiently polished to act as a good mirror. Thus the vast majority of industrially-used components comprise 'rough' surfaces. Similar issues with speckle and/or irregular beam deflection can occur when rough or smooth surfaces are subjected to mechanical vibrations.

Figure 1:
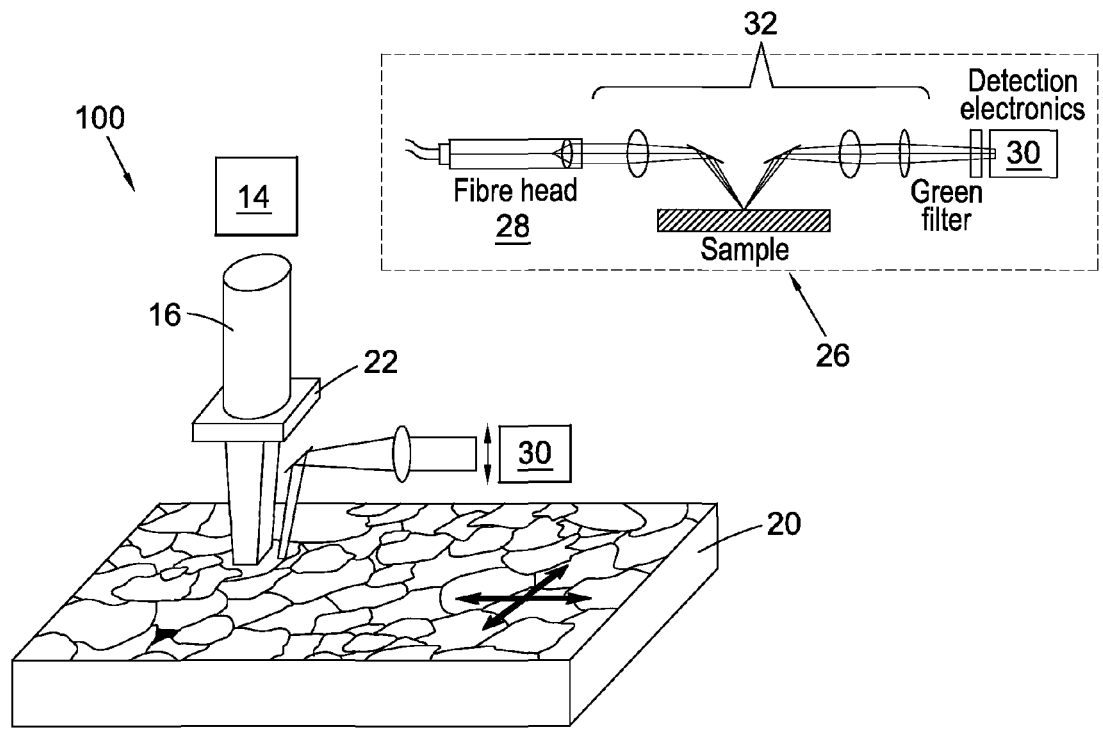
Figure 2:
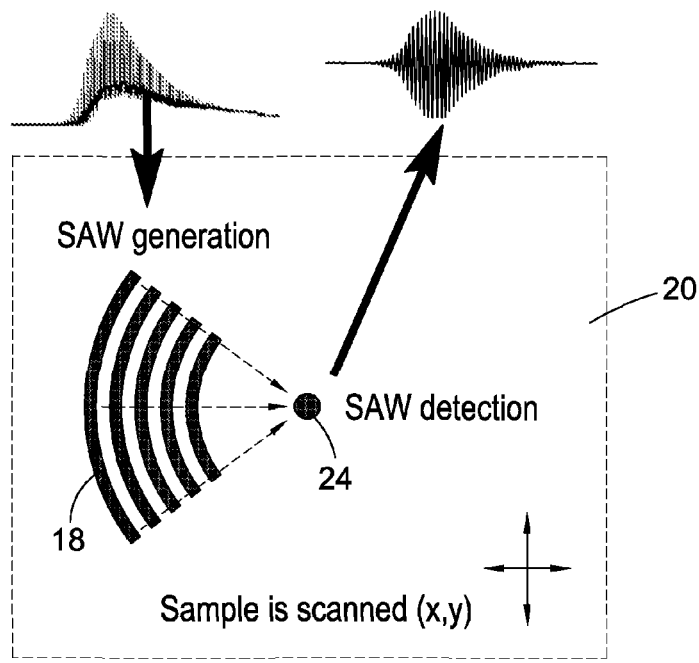

An optical evaluation system 100 which aims to address the above issues is shown in FIGS. 1 and 2.

The system 100 includes an excitation optical source 14, which is operable to produce a beam 16 of optical radiation in order to induce surface acoustic waves (SAWs) on the surface of a sample under test 20. A suitable excitation optical source would be an excitation laser, for example a Nd:YAG laser (neodymium-doped yttrium aluminium garnet laser).

The system further includes a detection system 26, which is shown more completely in the inset to FIG. 1. The detection system includes a detection optical source, in this case a detection laser 28, which is operable in use to direct a beam of optical radiation onto the surface of the sample 20 at a suitable location in the expected path of the SAWs. The detection beam is arranged to reflect from the surface of the sample onto an optical detector 30. The path of the detection beam and its reflection is controlled by detection optics 32.

In use, the excitation source is used to generate surface acoustic waves (SAWs) in the sample under test in any suitable way (e.g. by thermally heating the surface to cause expansion, or by ablation). The SAWs are then detected at the optical detector 30 via the reflection of the detection laser. The progress of the SAWs may then be analysed to obtain information about the surface of the sample under test at the point of reflection. An image of the surface of the sample may be built up by raster scanning the surface in a conventional way.

If required, the beam of optical radiation generated by the excitation laser 14 may be shaped to produce SAWs of a predefined shape using a suitable imaging means such as a spatial light modulator (SLM) 22. In the example shown the SLM 22 is arranged to image a regular grating of arbitrary spacing. The grating spacing can be adjusted during operation if required. We have found it desirable to match the grating spacing as closely as possible to the wavelength of the SAWs. We have also found it desirable to arrange the grating such that the SAWs come to a focus at a predetermined location 24. The detection laser 28 can then be positioned so as to image SAWs at the focus where maximum deflection is experienced. The optical illumination pattern used to assist in SAW generation is indicated in FIG. 2 at 18.

An optical detector 30 is shown schematically in FIG. 4 picture A. The optical detector 30 comprises a plurality of pixels 34. Each pixel comprises a photodiode 36 (see e.g. FIG. 4 picture C) which is operable to detect light incident on that pixel and to generate an electrical signal indicative of the intensity of that light.

The optical detector is arranged to be interactively configurable, in that it is able to alter its architecture in dependence on the light falling on each pixel. In particular, the signal generated by each pixel may be directed to one of a plurality of outputs. Which output is selected is dependent on the optical conditions in which the pixel finds itself. The conditions in which the pixel finds itself are determined with reference to another pixel of the array. Thus the plurality of pixels is grouped into a plurality of pixel pairs 38. For each pair, a comparison is made between the light intensity falling on a first pixel of a pair and a second pixel of the pair. This comparison influences the selection of output for the first pixel.

Because the detector is configurable, as described in more detail below, the arrangement of the pairs may be selected by a user if required. It will thus be appreciated that the 'pairs' referred to are not physical structures so much as associations between two pixels.

A typical pixel pair arrangement includes pairs in which the first and second pixels in any given pair are adjacent to one another. In the ultrasonics example discussed herein, we have found best results are achieved when the pairs are adjacent and arranged periodically (i.e. in the same spatial orientation—all in the same axis, which might be 'horizontal', or 'vertical'). The detector works most efficiently when neighbouring pairs overlap, so that the first pixel of one pair is the second pixel of an adjacent pair. Thus output to which the second pixel directs its intensity signal is determined based on a comparison with a different pixel than the first pixel, and also with respect to a different pair grouping.

The intensity comparisons between pixels are, in one example, performed substantially simultaneously (i.e. in parallel) with one another. This is more efficient than conducting the comparisons in series. Comparisons between pixel intensities are performed by comparators coupled between pixels, for example in the form of comparison electronics. Each pixel may be linked to more than one other pixel by a comparator, as this allows that pixel to form part of more than one pair. For example, the pixels may be arranged in a regular planar arrangement, such as a rectangular array, having two perpendicular axes, e.g. an x-axis and a y-axis. Each pixel of the array therefore has four pixels abutting it, two in the x-axis and two in the y-axis (excluding in this case diagonals). If comparison electronics are provided between the centre pixel and the four surrounding pixels a user is able to elect to arrange the pairs in alignment with the x-axis, or in alignment with the y-axis. The user may alter pair groupings and switch from one axis to the other as required. Providing four pair options allows for significant versatility without excessive complexity. However, further pair options might be provided for if required (e.g. comparison means might be provided between a pixel and diagonally adjacent pixels).

Typically, the detector includes a configuration mode, in which the architecture of the detector is configured using the selected pixel pair arrangement based on the optical radiation falling on the detector, and an experiment mode, in which the detector operates as configured in the configuration mode. In the configuration mode, the signals generated by each pixel of any given pixel pair are compared in the detector, e.g. by circuitry 40 present on the detector. The comparison is used to determine whether the intensity of light incident on the first pixel of a pair is higher than the intensity of light incident on the second pixel of that pair. If the intensity of light on the first pixel is higher than the intensity incident on the second pixel, the signal from the first pixel is directed to a first output. If the intensity of light on the first pixel is lower than the intensity incident on the second pixel, the signal from the first pixel is directed to a second, different, output.

Thus the detector is sensitive to light gradients at points across the pixel array (i.e. between the pairs of pixels). The detector can be reconfigured regularly, for example at the direction of a user or at pre-programmed intervals, to take into account changing optical conditions.

Figure 5:
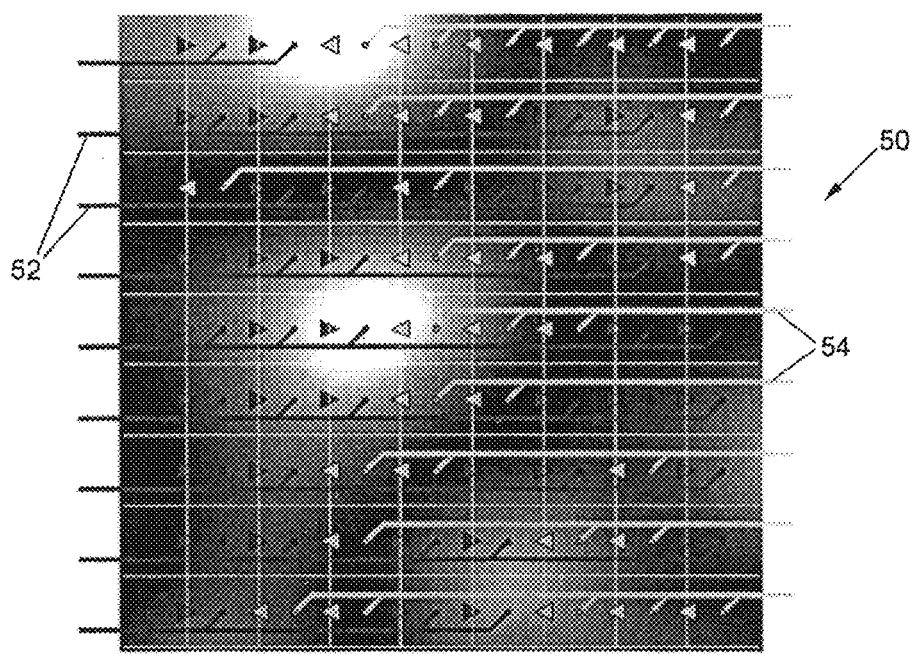
FIG. 5 depicts an optical detector in use during analysis of a rough surface.

Referring now to FIG. 5, a more detailed example of a configurable optical detector is described. The detector shown in FIG. 5 is sometimes referred to herein as a speckle knife edge detector (SKED), and includes an array of 32×32 active photodiode pixels (not all of which are visible in the figure). The detector also includes a row of dummy pixels along each edge of the array, as described in more detail below.

The optical detector 50 has two modes of operation: configure, and experiment, and the two modes are selectable by an external digital input. In configure mode, all photodiode outputs (in terms of an electrical current proportional to the light intensity) are isolated from each other. The relative intensity of light impinging on pairs of pixels (in this case the pairs are arranged horizontally, and overlap) is determined using an electrical current comparator, in order to determine which of the two pixels has more light falling on it. There is a comparator between each possible pair of horizontally adjacent pixels.

The detector 50 is arranged to measure changes in light intensity across the detector array. Between pairs of adjacent pixels, the chip calculates whether there is more light falling on the left, or the right (represented by the left and right arrows). If there is more light falling on the right, then the signal from the right hand pixel is sent to a first output (indicated by dark arrows, 52); if there is more light falling on the left, then the signal from the right hand pixel is sent to a second, different, output (indicated by light arrows, 54). The choice of output for the left pixel is determined in the same way, but by reference to the pixel on its left.

All the pixel pair comparisons are performed in parallel, so that all the signals from the positive gradient 'dark arrow' pixels are sent to the first output and summed, whilst all the signals from the negative gradient 'light arrow' pixels are sent to the second output and summed. In particular, the output of each comparator determines the setting of an electronic switch, which itself determines to which of two output connectors—A or B—the first pixel of each pair of photodiodes will be connected, once the output is in experiment mode.

Thus, in experiment mode, there will be a number of pixels connected to output A, and a number to output B. Those connected to output A will be those whose incident optical intensity was, during configuration, lower than the pixel to the right, those connected to output B will be those whose incident optical intensity was greater than the pixel to the right. There is an extra row, and an extra column, of "dummy" pixels at the edges of the array of pixels that are identical to the normal pixels but never have their output connect to the A or B outputs, so that comparisons can be made at the edges of the array.

The result during experiment mode is that the sum of all the dark arrow pixels 52 is subtracted from the sum of all the light arrow pixels 54. This results in a signal proportional to the horizontal movement of the speckles across the detector. The detector thus unravels the speckles to produce an output analogous to that of a conventional knife edge detector. Measurement of the intensity changes thus allows us to use the light reflected from the rough sample and reorganise it so that it behaves as if the reflection were from a smooth surface.

It is possible to switch between configure and experiment mode at a rate greater than 1000 times/second (i.e. >1 kHz), for example greater than 50 kHz. Configuration—where the chip adapts to the optical speckle—can take place in less than 5 microseconds, e.g. in around 1 microsecond or 0.1 microsecond.

The switch rate of the detector, its adaption speed, depends on (a) how quickly the electronic comparators can track the speckle, (b) the shortest time that the device must be in configuration mode to accurately record the speckle, and (c) how close in time the configuration can take place before the ultrasound is to be measured.

FIG. 10 illustrates how the configuration time can be established. The 'mode select' trace 60 (top trace) determines whether the detector is adapting to optical speckle (i.e. in configuration mode) or measuring ultrasound (i.e. in experiment mode). When the trace is high (in this case for around 100 ns) the detector is in configuration mode. When the trace is low (for the remainder of the time) the detector is in experiment mode.

In FIG. 10, the ultrasound signal is on the left, in the form of a noise burst from the change of mode state shown in the centre. Trace 0 is before any configure. Trace 1 is after the first configure slot (line 0). Trace 2 is after the second configure slot (line 1), and so on to trace 9. As can be seen, a 100 ns configuration time is sufficient to allow the detector to reconfigure appropriately.

FIG. 11 shows how the minimum time between configuration and measuring can be determined. In this case the mode select trace 60 shows a 1.4 microsecond configuration time. The ultrasound signal is on the right, in the form of a noise burst from the change of mode select state on the left. Trace 0 is the first configure after having all pixels set one way (no signal). The ultrasonic arrival time jitter is die to trigger jitter (triggered off previous event).

It can be seen that the duration of each measurement trace is less than 500 ns, meaning the configuration and measurement can take place less than 500 ns apart.

Figure 6:
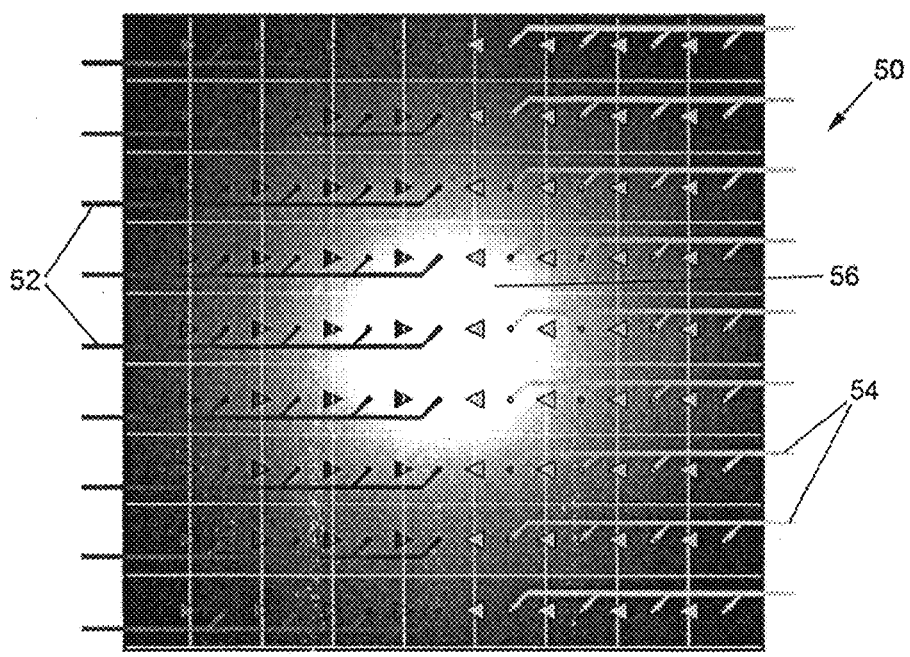
FIG. 6 depicts an optical detector in use during analysis of a smooth surface.

FIG. 6 shows a situation where the optical detector 50 is used to image a smooth surface (note the disc-like specular reflection 56). It can be seen that the pixels on the left are all directed to the same output, as signified by dark arrows 52, whilst the pixels on the right are all directed to the other, different, output, signified by light arrows 54. Thus the SKED behaves in an identical way to a conventional knife edge detector when evaluating a smooth surface.

Figure 7:
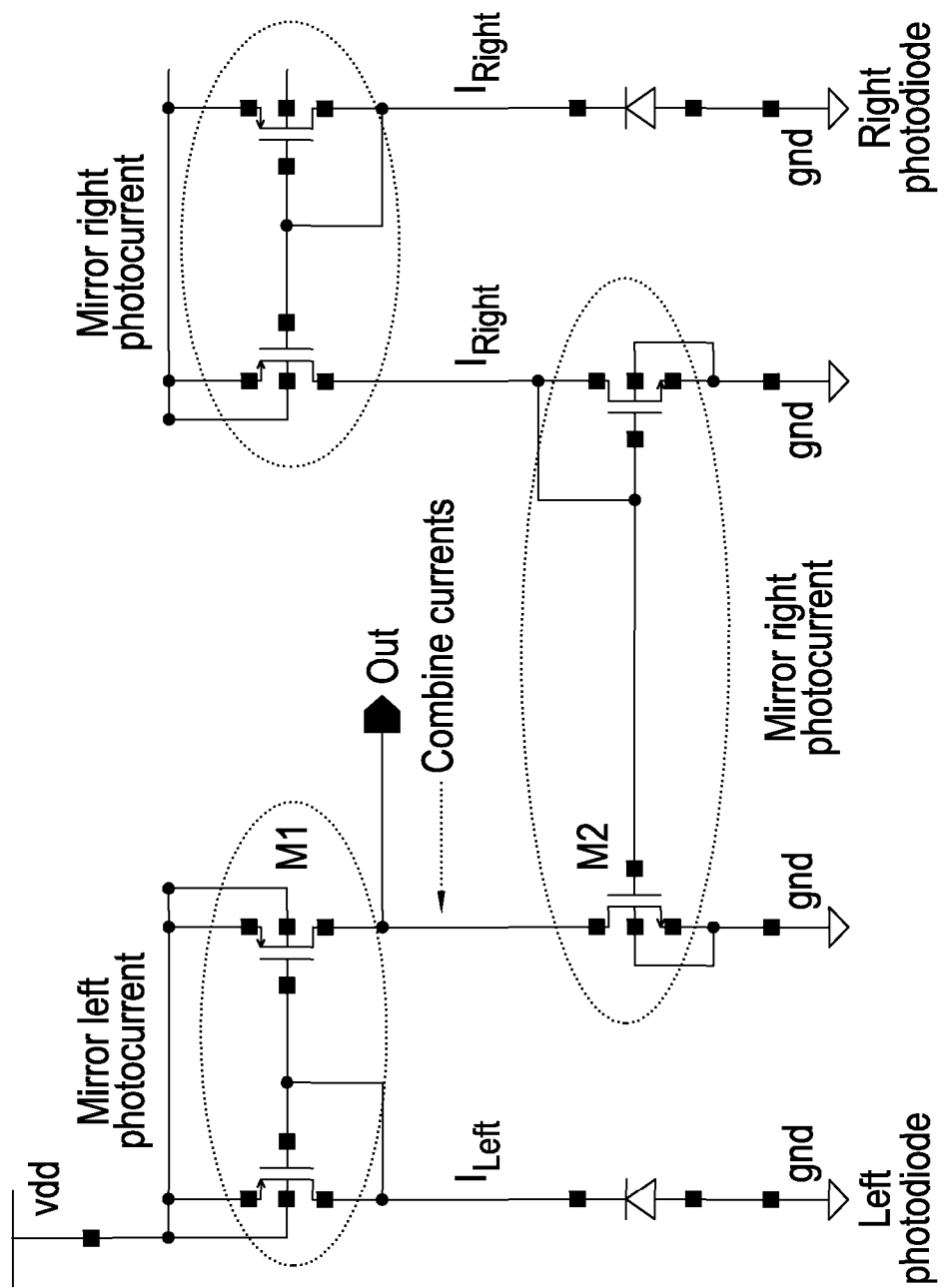
FIG. 7 is a circuit schematic for a current comparator.

FIG. 7 shows a simplified circuit schematic of how the signals indicative of incident light intensity in two adjacent pixels of a pair are compared. Each pixel includes a photodiode which is operable to generate the signal—an electrical current—which is proportional to the light intensity incident on that pixel. The current in the first, in this case right hand, photodiode (marked as $I_{Right}$) is mirrored twice using two current mirror circuits as shown. This duplicates the current flowing in the photodiode so that the same amount of current is flowing in the adjacent pairs of transistors. The second, in this case left hand, photodiode current (marked as $I_{Left}$) is mirrored once. At the wire marked "Combine currents", the left and right currents are connected together through transistors M1 and M2. It is important to note that there is nowhere else for the current in M1 and M2 to flow—the terminal Out here is a high impedance. If the current in the right hand photodiode is greater, M2 will try to sink more current than M1 is sourcing. Consequently, the voltage at the Out terminal will drop to a low voltage. If the left hand photocurrent is higher then the voltage at the Out terminal will rise to a high voltage. If both photocurrents are exactly equal, the voltage at the Out terminal will be at the mid point between the voltage rails. The output of this circuit is provided as an input to a voltage comparator. Thus, by setting the second input (the reference) to the voltage comparator to the mid point between the voltage rails, the output of the comparator will indicate which photodiode current is higher.

A circuit for a complete pixel is shown in FIG. 9. The circuit shown in FIG. 9 includes comparison means in the form of a current comparison circuit, and is suitable for use in a detector having two axes, e.g. x and y axes as discussed above, so that a comparison can be made in either axis (or both). As before, the pixel is operable to switch between first and second outputs, A and B, and the detector has two modes, configure and experiment.

During configure mode, each pixel compares its light intensity with the adjacent pixel. If the intensity is higher in the first pixel, it sets its output to A. If the light intensity in the adjacent pixel is higher, the first pixel sets its output to B.

During experiment mode, all pixel outputs A are tied together and all outputs B are tied together. This means that the chip outputs A and B represent the sum of the light intensity/photo current from the 'A' pixels and the 'B' pixels, respectively.

Each pixel contains a photodiode, which is the photo sensitive element in the pixel. During operation the photodiode is connected in one of three ways as controlled by three transmission gates (switches). If the "Mode" digital input to the pixel (indicated in FIG. 9 as "Measure") is held high, then the pixel is in configure mode and the photodiode is connected to the comparison circuitry.

The comparison circuitry consists of a current mirror that reproduces the photocurrent in two arms. In one of those arms the photocurrent is again reproduced to act as a current sink, with the other arm functioning as a current source. The outputs of these two mirrors are connected to the two adjacent pixels through transmission gates. One arm goes to the "next" photodiode for comparison and the other arm goes to the "previous" photodiode. This arrangement allows the comparison to happen in parallel across the chip. The "Axis" digital input allows the photodiodes to compare with to be chosen. If Axis is high, the comparison happens in a first, in this case horizontal, axis. If Axis is low, the comparison is in a second, in this case perpendicular, vertical, axis. This feature allows comparisons in both axes without requiring the detector to be moved. Comparisons between adjacent pixels is done by connecting the current source output of the pixel doing the comparison with the current sink output of the adjacent pixel, both through the respective transmission gates for the selected axis. The point between these two current mirrors is connected to the input of a voltage comparator. If the current in both the source and the sink is identical, a voltage of half the supply voltage is expected at the voltage comparator input. If the source current is higher, the voltage will increase and vice versa. A reference voltage (global for all pixels in the chip) is supplied to the second comparator input.

The comparator output is connected to a digital latch. When the pixel is placed in experiment mode, the digital latch retains the comparator value. The photodiode is also disconnected from the comparison circuit and connected to either output A or B ("ResLeft" and "ResRight" in the diagram) depending on the value of the digital latch.

There is further digital logic stored within the "pixel logic" block. This creates the ability to read the value of the digital latch at each pixel and take it off chip, as well as to program a value for the latch at each pixel from off chip. These are both useful additions to the design. Being able to see the configuration data is useful in an experimental environment because it gives an indication of the light on the sensor for example. Being able to program the configuration data allows the sensor to be programmed as a standard knife-edge detector or any other pattern. The configuration data can be programmed by setting "Force" high, setting "Select_n" low, setting the desired configuration value on "Direction" then briefly setting "ForceSet_n" low. The configuration data can be read by setting "Force" Low, setting "Select_n" low and reading the configuration data from "Direction".

Some experimental characterisation has been performed, and it has been found that a bandwidth of around 100 MHz can be achieved with a detector of the type described herein. It may be possible to increase this in future versions of the design, for example to 200 MHz.

FIG. 8 shows some experimental results achieved with an experimental optical detector having a bandwidth of approximately 20 MHz, which is adequate for many laser ultrasonic applications.

The experimental detector was tested using a laser ultrasound system called the O-SAM (all-optical scanning acoustic microscope), in which the generation laser excites surface acoustic waves at a frequency of 82 MHz. The experimental detector was compared against a standard knife edge detector (KED) on an optically rough aluminium surface. The pair of graphs in panel (1) of FIG. 8 shows the normalised amplitude of the 82 MHz waves as the sample is scanned over a distance of 2 mm. The output of the conventional KED is shown in picture A on the left, and is shown to fluctuate considerably, due to the changing speckle. In some sample locations, very little signal is present at all. The output of the experimental optical detector is shown in picture B on the right. It can be seen that the signal is much more constant, as the SKED adapts to the optical speckle at each sample location. The ideal behaviour would be a flat line at a height of 1.

Similar comparative behaviour is observed when the instrument is subject to ambient mechanical vibrations, which also changes the speckle pattern, as shown in panel (2) of FIG. 8, again with the KED on the right in picture C and the experimental detector on the left in picture D. Again, it can be seen that the new detector provides improved results. As before, the ideal behaviour would be a flat line with a height of 1.

The optical detectors described herein are able to operate as a drop in replacement for the conventional knife edge detectors, but are operable to obtain measurements on rough as well as smooth surfaces. Detector architecture (e.g. which of a plurality of outputs a pixel signal is directed/connected to) is configured interactively with reference to another pixel of the array, in response to local illumination conditions. Intensity gradients across pixel pairs are compared during the configuration. The detector can be reconfigured regularly, for example at pre-programmed intervals (e.g. once every 0.001 s, 0.01 s, 0.05 s or every 0.1 s), or in response to a user command.

A traditional knife edge detector measures beam deviations in a single axis, but the configurable detectors described herein are able to detect beam deviations in both the vertical and horizontal axes, based on a user controllable input. This means that measurements in both axes can be made without physically moving the device. It is also be possible to read out the configuration data from the device. This allows the user to obtain information about the roughness of their sample surface and determine whether the illumination and detector is correctly aligned. Configuration data can be stored, and also input, allowing a user to program the architecture of the detector directly if required, e.g. to operate in accordance with a previous configuration, or with a predefined pattern such as a conventional knife edge.

Although optical detectors have been described herein primarily with respect to laser ultrasonic applications, it will be appreciated that such sensors have utility in other applications, for example in situations where varying light levels mean that it is desirable to be able to control the sensitivity of a detector chip quickly and cheaply.

The invention claimed is:

1. An optical detector comprising:
   a plurality of pixels,
   comparison circuitry,
   a first output, and
   a second output,
   wherein each pixel comprises a photodiode operable to detect light incident on that pixel and to generate a signal indicative of an intensity of that light,
   wherein the plurality of pixels comprises a plurality of pixel pairs, and
   wherein the detector comprises a configuration mode in which, for each pixel pair, the comparison circuitry is operable to produce a comparison between the signal indicative of intensity generated by a first pixel of the pair and the signal indicative of intensity generated by a second pixel of the pair, and to connect the signal indicative of intensity generated by the first pixel to either the first output or the second output depending on the result of the comparison.

2. An optical detector as claimed in claim 1, wherein the plurality of pixels comprises an array, and wherein the signal indicative of intensity generated by each pixel in an active area of the array is connected to either the first output or the second output.

3. An optical detector as claimed in claim 2, wherein the detector further comprises an experiment mode in which the signals indicative of intensity received at the first output are summed to produce a first composite intensity signal, and the signals indicative of intensity received at the second output are summed to produce a second composite intensity signal.

4. An optical detector as claimed in claim 3, wherein, in the experiment mode, the second composite intensity signal is subtracted from the first composite intensity signal or the first composite intensity signal is subtracted from the second composite intensity signal.

5. An optical detector as claimed in claim 1, wherein, in the configuration mode, the comparison is performed simultaneously and in parallel over the plurality of pixel pairs.

6. An optical detector as claimed in claim 1, wherein each pair of pixels comprises a pair of adjacent pixels.

7. An optical detector as claimed in claim 1, wherein the arrangement of the pairs is periodic, such that the first pixel of each pair always has the same spatial relation with respect to the second pixel of that pair.

8. An optical detector as claimed in claim 6, wherein the pairs overlap, such that the first pixel in one pair comprises the second pixel in an adjacent pair.

9. An optical detector as claimed in claim 1, wherein the plurality of pixels is provided in a regular planar array having a first axis and a second axis which is perpendicular to the first axis, and wherein the comparison is performed based on pairs arranged in alignment with the first axis or the second axis.

10. An optical detector as claimed in claim 9, wherein the comparison can be switched between a comparison of pairs in the first axis and a comparison of pairs in the second axis.

11. An optical detector as claimed in claim 1, wherein the comparison circuitry comprises a comparator coupled between the first and second pixels of a respective pair.

12. An optical detector as claimed in a claim 11, wherein the comparator is provided between a first pixel and a plurality of neighbouring pixels, so that the intensity signal of the first pixel may be compared with the intensity signal of any one of the plurality of neighbouring pixels.

13. An optical detector as claimed in claim 11, wherein the comparison comprises a comparison of currents generated by the photodiodes of the first and second pixels of a respective pair.

14. An optical detector as claimed in claim 1, wherein the plurality of pixels comprises an array having an active area and a dummy area, wherein pixels of the dummy area do not have their intensity signals connected to the first or second output.

15. An optical evaluation system comprising a detection optical source, detection optics and an optical detector as claimed in claim 1.

16. An optical evaluation system as claimed in claim 15 further comprising an excitation optical source operable to generate sound waves in a sample under test.

17. An optical evaluation system as claimed in claim 16 further comprising optical imaging means such as a spatial light modulator to shape optical radiation generated by the excitation optical source.

18. An optical evaluation system as claimed in claim 17 wherein the optical imaging means is operable to shape the optical radiation so as to cause the sound waves to come to a focus.

19. A method of operating an optical detector having a plurality of pixels, comparison circuitry, a first output, and a second output, wherein each pixel comprises a photodiode operable to detect light incident on that pixel and to generate a signal indicative of an intensity of that light, the method comprising:

grouping a plurality of pixels into pairs, and operating the detector in a configuration mode in which, for each pixel pair, the signal indicative of intensity generated by a first pixel of the pair is compared with the signal indicative of intensity generated by a second pixel of the pair, and the signal indicative of intensity generated by the first pixel of the pair is connected to either the first output or the second output depending on the result of the comparison.

20. A method of operating an optical detector as claimed in claim 19, further comprising using the comparison to determine whether the intensity of light incident on the first pixel of the pair is higher than the intensity of light incident on the second pixel of the pair.

21. A method of operating an optical detector as claimed in claim 19, wherein the method further comprises summing the signals indicative of intensity received at the first output to produce a first composite intensity signal, and summing the signals indicative of intensity received at the second output to produce a second composite intensity signal.

22. A method of operating an optical detector as claimed in claim 21, further comprising subtracting the second composite intensity signal from the first composite intensity signal or subtracting the first composite intensity signal from the second composite intensity signal.

23. A method of operating an optical detector as claimed in claim 19 wherein the comparison is performed simultaneously and in parallel over the plurality of pixel pairs.

* * * * *